United States Patent [19]

Martel et al.

[11] 4,315,012
[45] Feb. 9, 1982

[54] 3-TETRAHALOETHYL-CYCLOPROPANE-1-CARBOXYLATE ESTERS

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 205,245

[22] Filed: Nov. 10, 1980

[30] Foreign Application Priority Data

Nov. 14, 1979 [FR] France .................. 79 28049

[51] Int. Cl.³ .................. A61K 31/44; C07D 213/55
[52] U.S. Cl. .................. 424/263; 546/270; 546/300; 546/302
[58] Field of Search .................. 546/302, 300, 270; 424/263

[56] References Cited

U.S. PATENT DOCUMENTS

| | | | |
|---|---|---|---|
| 3,711,486 | 1/1973 | Torba .................. | 546/302 |
| 4,163,787 | 8/1979 | Malhotra et al. .................. | 424/263 |
| 4,221,799 | 9/1980 | Van Heertum et al. .................. | 424/263 |
| 4,238,614 | 12/1980 | Henrick .................. | 546/301 |
| 4,248,875 | 2/1981 | Henrick .................. | 424/263 |

*Primary Examiner*—Alan L. Rotman
*Attorney, Agent, or Firm*—Hammond & Littell, Weissenberger and Muserlian

[57] ABSTRACT

Novel esters in the form of their stereoisomers or mixtures thereof of the formula

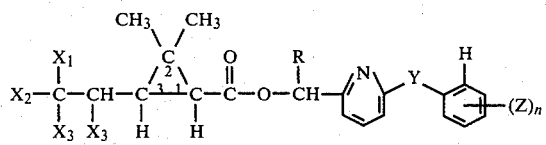

$X_1$ is selected from the group consisting of hydrogen, fluorine, chlorine and bromine, $X_2$ is selected from the group consisting of fluorine, chlorine and bromine, $X_3$ is selected from the group consisting of chlorine and bromine, each Z is independently selected from the group consisting of alkyl of 1 to 4 carbon atoms, alkoxy and alkylthio of 1 to 4 carbon atoms, alkylsulfonyl of 1 to 4 carbon atoms, —$CF_3$, 3,4-methylenedioxy, chlorine, fluorine and bromine, n is 0, 1 or 2, Y is selected from the group consisting of oxygen and sulfur and R is selected from the group consisting of hydrogen, —CN and ethynyl, the acid moiety having a structure selected from the group consisting of 1R, cis; 1S, cis; 1R, trans; and 1S, trans and the alcohol moiety having a configuration of (R), (S) or (RS) and the asymetric carbon in the 1-position of the 3-ethyl side chain exists in the form of isomer A and isomer B having insecticidal and acaricidal activity and their preparation.

55 Claims, No Drawings

3-TETRAHALOETHYL-CYCLOPROPANE-1-CARBOXYLATE ESTERS

STATE OF THE ART

Somewhat similar but different esters are described in French Pat. No. 2,383,927, German Pat. No. 2,829,329 and commonly assigned U.S. patent application Ser. No. 834,659 filed Sept. 19, 1977, now abandoned and U.S. Pat. No. 4,179,575.

OBJECTS OF THE INVENTION

It is an object of the invention to provide the novel esters of formula I and a novel process for their preparation.

It is another object of the invention to provide novel pesticidal compositions and to novel methods of combatting insects, acariens, nematodes and fungus.

These and other objects and advantages of the invention will become obvious from the following detailed description.

THE INVENTION

The novel esters of the invention are compounds in the form of their stereoisomers or mixtures thereof of the formula

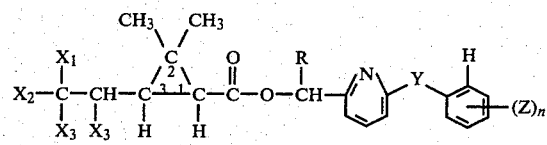

$X_1$ is selected from the group consisting of hydrogen, fluorine, chlorine and bromine, $X_2$ is selected from the group consisting of fluorine, chlorine and bromine, $X_3$ is selected from the group consisting of chlorine and bromine, each Z is independently selected from the group consisting of alkyl of 1 to 4 carbon atoms, alkoxy and alkylthio of 1 to 4 carbon atoms, alkylsulfonyl of 1 to 4 carbon atoms, —$CF_3$, 3,4-methylenedioxy, chlorine, fluorine and bromine, n is 0, 1 or 2, Y is selected from the group consisting of oxygen and sulfur and R is selected from the group consisting of hydrogen, —CN and ethynyl, the acid moiety having a structure selected from the group consisting of 1R, cis; 1S, cis; 1R, trans; and 1S, trans and the alcohol moiety having a configuration of (R), (S) or (RS) and the asymetric carbon in the 1-position of the 3-ethyl side chain exists in the form of isomer A and isomer B.

The esters of formula I exist in a number of isomeric forms since the cyclopropane carboxylic acid portion of the esters of formula I possesses generally 3 asymetric carbon atoms with asymetric carbon atoms in the 1- and 3-positions of the cyclopropane ring and the asymetric carbon in the 1-position of polyhalogenated ethyl side chain fixed in the 3-position of the cyclopropane ring. In the case of $X_1$, $X_2$ and $X_3$ being different from each other, a supplementary asymetric carbon atom exists in the 2-position of the polyhalogenated ethyl side chain.

The alcohol of the formula

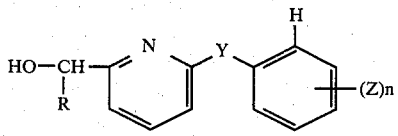

forming the alcohol portion of the esters of formula I generally contain an asymetric carbon atom which is a supplementary cause of stereoisomerism. Examples of alkyl groups in Z as well as the alkyl portion of alkoxy, alkylthio and alkylsulfonyl are methyl, ethyl, propyl, isopropyl, n-butyl, sec-butyl and tert.-butyl.

The esters of formula I encompass within the definition given the X substituents give compounds with a combination of different stereoisomers of the coupling acid with stereoisomers of the coupling alcohol with the asymetric carbon being either racemic or optically active. In the case where $X_1$ and $X_2$ are identical, the steric configuration is determined by the asymetrical carbon atoms in the 1- and 3-positions of the cyclopropane ring while the determined structure of the alcohol moiety is due to the asymetric carbon, the two diastereoisomeric forms of the esters I or the corresponding carboxylic acids due to the existence of an asymetric carbon atom in the 1-position of the ethyl side chain when it exists. Their existence may be effectively characterized especially by their NMR spectrum and/or the velocity of migration in thin layer chromatography.

The isomers may be separated and isolated in a pure state by known means, especially chromatography. The two diastereoisomers are named in a known fashion as isomers A and B. More generally, known physical methods are used for the separation of the different isomers of formula I and these are chromatography and crystallization especially.

Among the preferred compounds of formula I are those wherein R is cyano, those wherein Y is oxygen, those wherein n is 0, those wherein the acid moiety has the dl cis or dl trans structure, those wherein the acid moiety has the 1R, cis or 1R, trans structure, those wherein $X_1$ and $X_2$ are chlorine, those wherein $X_3$ is bromine and those wherein $X_1$, $X_2$ and $X_3$ are all bromine.

Examples of specific preferred compounds of the invention are (R)α-cyano-6-phenoxy-2-pyridyl-methyl 1R, trans 2,2-dimethyl-3-(1,2,2,2-tetrabromoethyl)-cyclopropane-1-carboxylate, (S)α-cyano-6-phenoxy-2-pyridyl-methyl 1R, trans 2,2-dimethyl-3-(1,2,2,2-tetrabromoethyl)-cyclopropane-1-carboxylate, (R)α-cyano-6-phenoxy-2-pyridyl-methyl 1R, cis 2,2-dimethyl-3-(1,2,2,2-tetrabromoethyl)-cyclopropane-1-carboxylate, (S)α-cyano-6-phenoxy-2-pyridyl-methyl 1R, cis 2,2-dimethyl-3-(1,2,2,2-tetrabromoethyl)-cyclopropane-1-carboxylate, (R)α-cyano-6-phenoxy-2-pyridyl-methyl 1R, trans 2,2-dimethyl-3-(1,2-dibromo-2,2-dichloroethyl)-cyclopropane-1-carboxylate, (S)α-cyano-6-phenoxy-2-pyridyl-methyl 1R, trans, 2,2-dimethyl-3-(1,2-dibromo-2,2-dichloroethyl)-cyclopropane-1-carboxylate, (S)α-cyano-6-phenoxy-2-pyridyl-methyl 1R, cis 2,2-dimethyl-3-(1,2-dibromo-2,2-dichloroethyl)-cyclopropane-1-carboxylate, (R)α-cyano-6-phenoxy-2-pyridyl-methyl 1R, cis 2,2-dimethyl-3-(1,2dibromo-2,2-dichloroethyl)-cyclopropane-1-carboxylate, (RS)α-cyano-6-phenoxy-2-pyridyl-methyl 1R, trans 2,2-dimethyl-3-(1,2,2,2-tetrabromoethyl)-cyclopropane-1-carboxylate, (RS)α-cyano-6-phenoxy-2-pyridyl-methyl 1R, cis 2,2-dimethyl-3-(1,2,2,2-tetrabromoethyl)-cyclopropane-1carboxylate, (RS)α-cyano-6-phenoxy-2-pyridyl-methyl 1R, trans 2,2-dimethyl-3-(1,2-dibromo-2,2-dichloroethyl)-cyclopropane-1-carboxylate, (RS)α-cyano-6-phenoxy-2-pyridyl-methyl 1R, cis 2,2-dimethyl-3-(1,2-dibromo-2,2-dichloroethyl)-cyclopropane-1-carboxylate and (RS)α-cyano-6-phenoxy-2-pyridyl-methyl dl cis 2,2-dimethyl-3-(1,2dibromo-2,2-dichloroethyl)-cyclopropane-1-carboxylate.

Besides the esters of the formula I, the corresponding cyclopropane carboxylic acids of 1R, cis or 1R, trans structure are preferred for the esters including the following: 2,2-dimethyl-3-(1,2-dichloro-2,2-dibromoethyl)-cyclopropane-1-carboxylic acids, 2,2-dimethyl-3-(1,2,2,2-tetrachloroethyl)-cyclopropane-1-carboxylic acids, 2,2-dimethyl-3-(1,2-dichloro-2,2-difluoroethyl)-cyclopropane-1-carboxylic acids, 2,2-dimethyl-3-(1,2-dibromo-2,2-dichloroethyl)-cyclopropane-1-carboxylic acids, 2,2-dimethyl-3-(1,2-dibromo-2,2-difluoroethyl)-cyclopropane-1-carboxylic acids, 2,2-dimethyl-3-(1,2,2,2-tetrabromoethyl)-cyclopropane-1-carboxylic acids, 2,2-dimethyl-3-(1,2,2-tribromoethyl)-cyclopropane-1-carboxylic acids, 2,2-dimethyl-3-(1,2-dichloro-2-bromoethyl)-cyclopropane-1-carboxylic acids, 2,2-dimethyl-3-(1,2,2-trichloroethyl)-cyclopropane-1-carboxylic acids, 2,2-dimethyl-3-(1,2-dibromo-2-chloroethyl)-cyclopropane-1-carboxylic acids, 2,2-dimethyl-3-(1,2-dichloro-2-fluoroethyl)-cyclopropane-1-carboxylic acids, 2,2-dimethyl-3-(1,2-dibromo-2-fluoroethyl)-cyclopropane-1-carboxylic acids, 2,2-dimethyl-3-(1,2,2-trichloro-2-fluoroethyl)-cyclopropane-1-carboxylic acids, 2,2-dimethyl-3-(1,2-dibromo-2-chloro-2-fluoroethyl)-cyclopropane-1-carboxylic acids and 2,2-dimethyl-3-(1,2,2-tribromo-2-chloroethyl)-cyclopropane-1-carboxylic acids.

It is well understood all the esters of formula I can by derived from cyclopropane carboxylic acids of (1S, cis) or (1S, trans) structure. In this case, the esters of formula I may include cyclopropane carboxylic acids of dl cis structure [equimolar mixture of (1R, cis) and (1S, cis) structures] or dl trans structure [equimolar mixture of (1R, trans) and (1S, trans) structures] or a mixture of acids of dl cis or dl trans structures.

As has been indicated, the preferred esters of formula I are those where the acid moiety of the esters has the (1R, cis) or (1R, trans) structure as well as those wherein the acid moiety has the dl cis or dl trans structure and mixtures of esters wherein the acid moiety is dl cis or dl trans structure.

The novel process of the invention for the preparation of the esters of formula I comprises reacting an ester of the formula

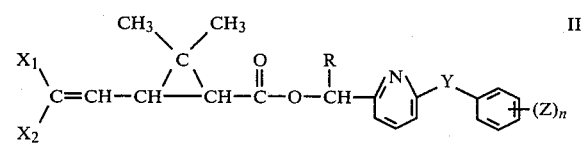

wherein $X_1$, $X_2$, R, Z and n have the above definitions which may be in one of its stereoisomeric forms or a mixture of stereoisomeric forms with a chlorination or bromination agent capable of fixing $Cl_2$ or $Br_2$ in the double bond of the vinyl side chain of the cyclopropane carboxylic and separating by physical means, if desired, the desired isomer.

Examples of suitable chlorination or bromination agents are chlorine and bromine and the reaction is preferably effected in an organic solvent not reactive with chlorine or bromine such as acetic acid, carbon tetrachloride, chloroform and methylene chloride.

The starting esters of formula II may be prepared by esterifying the corresponding dihalovinyl cyclopropane carboxylic acid or a functional derivative thereof with an alcohol of formula IV by known methods which, if desired, may be separated by known methods into its individual isomers. The compounds of formula II wherein R is cyano may also be obtained by the known method of phase transfer by reacting 6-phenoxy-2-picolinic aldehyde with a compound capable of generating cyanide ions and with the desired dihalovinyl carboxylic acid or a functional derivative thereof and optionally separating the desired isomer by physical methods. By this type of process, it is possible, for example, to obtain esters of the (R) or (S) configuration due to the alcohol moiety.

Another process of the invention for the preparation of the esters of formula I comprises reacting an acid of the formula

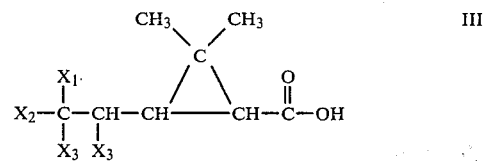

wherein $X_1$, $X_2$ and $X_3$ have the above definitions or a functional derivative thereof in one of its stereoisomeric forms or a mixture of stereoisomeric forms with an alcohol of formula IV and, if desired, separating by physical means the desired isomeric form.

The cyclopropane carboxylic acids of formula III and their functional derivatives may be prepared by the processes of French Pat. Nos. 2,398,714 and 2,398,041. The functional derivatives of the acids of formula III for reaction with the alcohol of formula IV or its functional derivatives are preferably the acid chloride, the acid anhydride, mixed acid anhydride and the lower alkyl esters for trans esterification or the metal salt such as alkali metal, silver or organic amine salts such as the triethylamine salt. The functional derivative of the alcohol of formula IV is preferably the chloride or bromide or sulfonate of the alcohol. Other classical procedures of esterification of the acid of formula III or its functional derivatives with an alcohol of formula IV or its functional derivatives may be used without departing from the scope of the invention.

Another process of the invention for the preparation of esters of formula I wherein R is cyano comprises effecting a phase transfer catalysis of an acid of formula III or a functional derivative thereof either in its stereoisomeric form or a mixture of its stereoisomeric forms with a compound capable of generating cyanide ions and with a compound of the formula

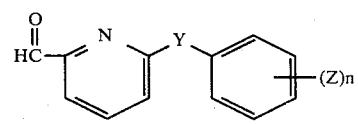

wherein Y, Z and n have the above definitions in the presence of a basic catalyst in an aqueous medium and in the presence of a partially water-miscible solvent and separating, if desired, by physical means the desired isomer.

In a preferred embodiment of the latter process, the compound capable of generating cyanide ions is sodium cyanide, the basic catalyst is tetradecyl trimethyl ammonium bromide and the partially water-miscible solvent is toluene.

It is understood that the esters of formula II can exist in numerous isomeric forms due to the asymetric carbons in the 1- and 3-position of the cyclopropane ring and the existence of an asymetric carbon in the alcohol moiety. Moreover, the acid of formula III and its functional derivatives also exists in diverse isomeric forms due to the asymetric carbons in the 1- and 3-position of the cyclopropane ring.

The novel pesticide compositions of the invention are comprised of a pesticidally effective amount of at least one ester of formula I and an inert carrier. The compositions may also contain one or more other pesticidal agents and may be used in the form of powders, granules, suspensions, emulsions, solutions, aerosol solutions, combustible strips, baits or other preparations used for preparation of this type.

The compositions may also contain classical pyrethrinoid synergists such as 1-(2,5,8-trioxadodecyl- 2-propyl-4,5-methylenedioxy)-benzene or piperonyl butoxide and N-(2-ethylheptyl)-bicyclo-[2,2-1]-5-heptene-2,3-dicarboximide and piperonyl-bis-2-(2-n-butoxyethoxy)-ethyl-acetal or tropital.

Examples of the inert carriers are a vehicle and/or a nonionic surface active agent to ensure a uniform dispersions of the components of the mixture. The vehicle may be a liquid such as water, alcohol, hydrocarbons or other organic solvents, a mineral, animal or vegetable oil or a powder such as talc, clays, silicates or kieselguhr or a combustible solid such as tabu powder or pyrethrum residue.

The pesticidal compositions of the invention are useful as insecticides useful against lice, lepidoptera larvae, coleoptera and are generally useful in the agricultural field. They are also useful as insecticides for the domestic field such as houseflies. Tests have shown the compositions to be effective against houseflies, Spodoptera littoralis, Epilachna varivestris and cracivora aphides.

The compositions are also useful as acaricides against acarien parasites of vegetables as evidenced by their activity against Tetranichus urticae and as acaricides for animal acariens which permit their use to fight against parasitic ixodes of warm-blooded animals either externally or generally. The compositions have fungicidal and nematocidal activity as well.

When used as insecticides or acaricides, the compositions preferably contain 0.005 to 10% by weight of the compounds of formula I. The nematocidal compositions preferably contain 300 to 500 g/l of the esters of formula I and are applied at the rate of 1 to 100 g of active ingredient per hectare. The fungicidal compositions of the invention preferably contain 10 to 95% by weight of the said esters.

The novel method of the invention for combatting pests comprises contacting the pests with a pesticidally effective amount of at least one compound of formula I. The pests may be contacted by direct application of the compound or by ingestion thereof or by application to the locus which the pest comes in contact with.

In the following examples there are described several preferred embodiments to illustrate the invention. However, it is to be understood that the invention is not intended to be limited to the specific embodiments.

EXAMPLE 1

(R,S)α-cyano-6-phenoxy-2-pyridyl-methyl dl cis trans 2,2-dimethyl-3-[1-(R,S)-2-dibromo-2,2-dichloroethyl]-cyclopropane-1-carboxylate 0.040 g of benzoyl peroxide was added to a mixture of 4.37 g of (R,S)α-cyano-6-phenoxy-2-pyridyl-methyl dl cis trans 2,2-dimethyl-3-(2,2-dichlorovinyl)-cyclopropane-1-carboxylate otherwise known as (R,S)α-cyano-6-phenoxy-2-pyridylmethyl (1R, 3RS; 1SR, 3SR; 1RS, 3SR; 1SR, 3RS) 2,2-dimethyl-3-(2,2-dichlorovinyl)-cyclopropane-1-carboxylate and 40 ml of carbon tetrachloride and then a solution of 1.63 g of bromine in 10 ml of carbon tetrachloride was added thereto over one hour at 0° C. with irridation with a lamp. The mixture was stirred at 0° C. with irridation for 90 minutes and was then evaporated to dryness under reduced pressure. The residue was chromatographed over silica gel and was eluted with a 7-3 chloroform-petroleum ether mixture to obtain 2.6 g of (R,S) α-cyano-6-phenoxy-2-pyridyl-methyl dl cis trans 2,2-dimethyl-3-[1-(R,S), 2-dibromo-2,2-dichloroethyl]-cyclopropane-1-carboxylate.

Analysis: $C_{21}H_{18}Br_2Cl_2N_2O_3$; molecular weight=577.1 Calculated: %C 43.70; %H 3.14; %Br 27.69; %Cl 12.28; %N 4.85. Found: %C 44.0; %H 3.4; %Br 27.4; %Cl 12.2; %N 4.8.

IR Spectrum (chloroform):

Absorption at 1745 cm$^{-1}$ (ester carbonyl); at 1590-1573-1409 cm$^{-1}$ (aromatic ring); at 1391-1381 cm$^{-1}$ (geminal methyls).

NMR Spectrum (deuterochloroform):

Peaks at 1.21 to 1.37 ppm (hydrogens of geminal methyls); at 1.71 to 2.5 ppm (1- and 3-hydrogens of cyclopropyl); at 4.25-4.42 and 4.42-4.58 ppm (1-hydrogen of ethyl); at 6.38-6.40 ppm (hydrogen on carbon attached to CN); at 6.4-7.03 ppm (5-hydrogen of pyridyl); at 7.08 to 7.67 ppm (hydrogens of phenyl); 7.74 to 8.0 ppm (3-and 4-hydrogens of pyridyl).

Using the same procedure starting with the dl cis and the dl trans equivalents, there was obtained (RS)α-cyano-6-phenoxy-3-pyridyl-methyl dl cis 2,2-dimethyl-3-(1RS)-2-dibromo-2,2-dichloro-ethyl)-cyclopropane-1-carboxylate and (RS)α-cyano-6-phenoxy-2-pyridyl-methyl dl trans 2,2-dimethyl-3-(1RS), 2-dibromo-2,2-dichloroethyl)-cyclopropane-1-carboxylate.

EXAMPLE 2

(R,S)α-cyano-6-phenoxy-2-pyridyl-methyl 1R, trans 2,2-dimethyl-3-(1,2-dibromo-2,2-dichloroethyl)-cyclopropane-1-carboxylate STEP A: (R,S)α-cyano-6-phenoxy-2-pyridyl-methyl 1R, trans 2,2-dimethyl-3-(2,2-dichlorovinyl)-cyclopropane-1-carboxylate A solution of 72 g of 6-phenoxy-2-picolinic aldehyde, 0.360 g of tetradecyl trimethylammonium bromide, 84.7 g of 1R, trans 2,2-dimethyl-3-(2,2-dichlorovinyl)-cyclopropane-1-carboxylic acid chloride and 290 ml of toluene (the acid chloride was added to the solution last) was slowly added at 23° C. to a mixture of 0.360 g of tetradecyl trimethylammonium bromide, 19.9 g of sodium cyanide and 216 ml of water and the mixture was stirred under an inert atmosphere at 23° C. for 21 hours. The decanted organic phase was washed with water, dried and evaporated to dryness under reduced pressure. Isopropanol was added to the residue and the mixture was evaporated to dryness to obtain 158 g of (R,S)α-cyano-6-phenoxy-2-pyridyl-methyl 1R, trans 2,2-dimethyl-3-(2,2-dichlorovinyl)-cyclopropane-1-carboxylate.

STEP B: (RS)α-cyano-6-phenoxy-2-pyridyl-methyl 1R, trans 2,2-dimethyl-3-(1,2-dibromo-2,2-dichloroethyl)-cyclopropane-1-carboxylate Using the procedure of Example 1, the product of Step A was brominated to obtain (RS)α-cyano-6-phenoxy-2-pyridyl-methyl 1R, trans 2,2-dimethyl-3-(1,2-dibromo-2,2-dichloroethyl)-cyclopropane-1-carboxylate which was separated by chromatography into the corresponding stereiosomers of the alcohol moiety.

EXAMPLE 3

(R)α-cyano-6-phenoxy-2-pyridyl-methyl 1R, trans 2,2-dimethyl-3-(1,2-dibromo-2,2-dichloroethyl)-cyclopropane-1-carboxylate STEP A: (R)α-cyano-6-phenoxy-2-pyridyl-methyl 1R, trans 2,2-dimethyl-3-(2,2-dichlorovinyl)-cyclopropane-1-carboxylate 158 g of the product of Step A of Example 2 were crystalized from isopropanol to obtain 75.2 g of (R)α-cyano-6-phenoxy-2-pyridyl-methyl 1R, trans 2,2-dimethyl-3-(2,2dichlorovinyl)-cyclopropane-1-carboxylate with a melting point of 102° C. and a specific rotation of $[\alpha]_D^{20} = -8°$ (c=3% in toluene).

Analysis: $C_{21}H_{17}O_3N_2Cl_2$; molecular weight=417.29. Calculated: %C 60.44; %H 4.34; %N 6.71; %Cl 16.99. Found: %C 60.6; %H 4.3; %N 6.7; %C 17.3.

NMR Spectrum (deuterochloroform):
Peaks at 1.23-1.32 ppm (hydrogens of geminal methyls); at 1.65-1.73 ppm (1-hydrogen of cyclopropyl); at 2.17-2.25-2.30-2.38 ppm (3-hydrogen of cyclopropyl); at 5.53-5.67 ppm (ethylenic hydrogen); at 6.32 ppm (hydrogen on carbon attached on CN).

STEP B: (R)α-cyano-6-phenoxy-2-pyridyl-methyl 1R, trans 2,2-dimethyl-3-(1,2-dibromo-2,2-dichloroethyl)-cyclopropane-1-carboxylate Using the procedure of Example 1, the product of Step A was brominated to obtain (R)α-cyano-6-phenoxy-2-pyridyl-methyl 1R, trans 2,2-dimethyl-3-(1,2-dibromo-2,2-dichloroethyl)-cyclopropane-1-carboxylate with a melting point of ≃110° C. and a specific rotation of $[\alpha]_D^{20} = -27°$ (c=1% in benzene).

Analysis: $C_{21}H_{18}Br_2Cl_2N_2O_3$; molecular weight=577.11. Calculated: %C 43.70; %H 3.14; %Br 27.69; %Cl 12.28; %N 4.85. Found: %C 43.9; %H 3.2; %Br 28.0; %Cl 12.7; %N 5.0.

NMR Spectrum (deuterochloroform):
Peaks at 1.31-1.38 ppm (hydrogens of geminal methyls); at 1.70-1.79 ppm (1-hydrogen of cyclopropyl ring); at 4.38-4.55 ppm and 4.30-4.38 ppm (1-hydrogen of ethyl—shows existence of 2 diastereoisomers); at 6.30 ppm (hydrogen on carbon attached to CN); at 6.80-6.95 ppm (3- or 5-hydrogens of pyridyl); at 7.61-7.75-7.77 ppm (4-hydrogen of pyridyl).

EXAMPLE 4

(S)α-cyano-6-phenoxy-2-pyridyl-methyl 1R, trans 2,2-dimethyl-3-(1,2-dibromo-2,2-dichloroethyl)-cyclopropane-1-carboxylate STEP A: (S)α-cyano-6-phenoxy-2-pyridyl-methyl 1R, trans 2,2-dimethyl-3-(2,2-dichlorovinyl)-cyclopropane-1-carboxylate The mother liquors from the crystallization of Step A of Example 3 were evaporated to dryness under reduced pressure and the residue was chromatographed over silica gel. Elution with a mixture of petroleum ether (b.p.=35°-70° C.)-isopropyl ether yielded 38.68 g of (S)α-cyano-6-phenoxy-2-pyridyl-methyl 1R, trans 2,2-dimethyl-3-(2,2-dichlorovinyl)-cyclopropane-1-carboxylate with a specific rotation of $[\alpha]_D^{20} = +20.5°$ (c=4% in toluene).

NMR Spectrum (deuterochloroform):
Peaks at 1.20-1.24 ppm (hydrogens of geminal methyls); at 1.65-1.74 ppm (1-hydrogen of cyclopropane); at 2.2-2.28-2.40-2.42 ppm (3-hydrogen of cyclopropyl); at 5.55-5.68 ppm (ethylenic hydrogen); at 6.32 ppm (hydrogen on carbon attached on CN); at 6.83-7.9 ppm (aromatic ring).

STEP B: (S)α-cyano-6-phenoxy-2-pyridyl-methyl 1R, trans 2,2-dimethyl-3-(1,2-bromo-2,2-dichloroethyl)-cyclopropane-1-carboxylate Using the procedure of Example 1, the product of Step A was brominated to obtain (S)α-cyano-6-phenoxy-2-pyridyl methyl 1R, trans 2,2-dimethyl-3-(1,2-bromo-2,2-dichloroethyl)-cyclopropane-1-carboxylate with a specific rotation of $[\alpha]_D^{20} = -4°$ (c=0.5% in benzene).

Analysis: $C_{21}H_{18}Br_2Cl_2N_2O_3$; molecular weight=577.11. Calculated: %C 43.70; %H 3.14; %Br 27.69; %Cl 12.28; %N 4.85. Found: %C 44.3; %H 3.1; %Br 27.3; %Cl 12.4; %N 4.18.

NMR Spectrum (deuterochloroform):
Peaks at 1.20-1.33 ppm and 1.27-1.33 ppm (hydrogens of geminal methyls); at 1.68-1.77 ppm and 1.96-2.36 ppm (1- and 3-hydrogens of cyclopropyl); at 4.18-4.35 ppm and 4.35-4.51 ppm (1-hydrogen of ethyl chain); at 6.30 ppm (hydrogen on carbon attached to —CN); at 6.80-6.93 ppm (3- or 5-hydrogen of pyridyl); at 7.61-7.73-7.85 ppm (4-hydrogen of pyridyl).

EXAMPLE 5

(RS)α-cyano-6-phenoxy-2-pyridyl-methyl 1R, cis 2,2-dimethyl-3-(1,2-dibromo-2,2-dichloroethyl)-cyclopropane-1-carboxylate STEP A: (RS)α-cyano-6-phenoxy-2-pyridyl-methyl 1R, cis 2,2-dimethyl-3-(2,2-dichlorovinyl)-cyclopropane-1-carboxylate 1.352 g of sodium cyanide and 0.025 g of tetradecyl trimethylammonium bromide were added to 15 ml of water and a solution of 4.9 g of 6-phenoxy-2-picolinic aldehyde, 0.025 g of tetradecyl trimethylammonium bromide, 6.15 g of 1R cis 2,2-dimethyl-3-(2,2-dichlorovinyl)-cyclopropane-1-carboxylic acid chloride and 20 ml of toluene was slowly added at 25° C. to the mixture. The mixture was stirred under an inert atmosphere at 23° C. for 15 hours and was then allowed to stand. The decanted organic phase was washed with water and the combined aqueous phases were washed with toluene and were evaporated to dryness under reduced pressure to obtain 10.8 g of raw (RS)α-cyano-6-phenoxy-2-pyridyl-methyl 1R, cis 2,2-dimethyl-3-(2,2-dichlorovinyl)-cyclopropane-1-carboxylate.

NMR Spectrum (deuterochloroform):
Peaks at 1.80-1.90-1.93 ppm (hydrogens of geminal methyls and hydrogen of methyl); at 2.83-3.5 ppm (hydrogens of cyclopropyl); at 9.17-9.36 ppm (ethylenic hydrogen in vinyl chain); at 9.48 ppm (hydrogen on carbon α to —CN); at 10.3-10.46-11.5-11.7-11.8 ppm (pyridinic ring); at 10.7–11.3 ppm (other aromatic hydrogens).

STEP B: (RS)α-cyano-6-phenoxy-2-pyridyl-methyl 1R, cis 2,2-dimethyl-3-(1,2-dibromo-2,2-dichloroethyl)-cyclopropane-1-carboxylate Using the procedure of Example 1, the product of Step A was brominated to obtain (RS)α-cyano-6-phenoxy-2-pyridyl-methyl 1R, cis 2,2-dimethyl-3-(1,2-dibromo-2,2-dichloroethyl)-cyclopropane-1-carboxylate which was separated by chromatography into the corresponding diastereoisomers of the asymmetric carbon of the alcohol moiety.

EXAMPLE 6

(R)α-cyano-6-phenoxy-2-pyridyl-methyl 1R, cis 2,2-dimethyl-3-(1,2-dibromo-2,2dichloroethyl)-cyclopropane-1-carboxylate STEP A: (R)α-cyano-6-phenoxy-2-pyridyl-methyl 1R, cis 2,2-dimethyl-3-(2,2-dichlorovinyl)-cyclopropane-1-carboxylate 10.4 g of the raw product of Step A of Example 5 were pressure chromatographed over silica gel and was eluted with an 8-2 petroleum ether (b.p.=35°–70° C.)-isopropyl ether mixture to obtain 4.812 g of (R)α-cyano-6-phenoxy-2-pyridyl-methyl 1R, cis 2,2-dimethyl-3-(2,2-dichlorovinyl)-cyclopropane-1-carboxylate with a specific rotation of $[\alpha]_D^{20} = -17°$ (c=4% in toluene).

NMR Spectrum (deuterochloroform):

Peaks at 1.29 ppm (hydrogens of geminal methyls); at 6.32 ppm (hydrogen on carbon attached to —CN). Chromatography of 4.75 g of the product over silica gel and elution with methylene chloride yielded 3.992 g of the purified product.

Analysis: $C_{21}H_{18}O_3N_2Cl_2$; molecular weight=417.89. Calculated: %C 60.44; %H 4.34; %N 6.71; %Cl 16.99. Found: %C 60.3; %H 4.3; %N 6.5; %Cl 17.2.

STEP B: (R)α-cyano-6-phenoxy-2-pyridyl-methyl 1R, cis 2,2-dimethyl-3-(1,2-dibromo-2,2-dichloroethyl)-cyclopropane-1-carboxylate Using the procedure of Example 1, the product of Step A was brominated to obtain (R)α-cyano-6-phenoxy-2-pyridyl-methyl 1R, cis 2,2-dimethyl-3-(1,2-dibromo-2,2-dichloroethyl)-cyclopropane-1-carboxylate with a specific rotation of $[\alpha]_D^{20} = -44°$ (c=0.5% in benzene).

IR Spectrum (chloroform):

Absorption at 1742 cm$^{-1}$ (ester carbonyl); at 1593, 1574 cm$^{-1}$, 1490 cm$^{-1}$ and 1450 cm$^{-1}$ (aromatic ring); at 1392 cm$^{-1}$ and 1383 cm$^{-1}$ (geminal methyls).

EXAMPLE 7

(S)α-cyano-6-phenoxy-2-pyridyl-methyl 1R, cis 2,2-dimethyl-3-(1,2-dibromo-2,2-dichloroethyl)-cyclopropane-1-carboxylate STEP A: (S)α-cyano-6-phenoxy-2-pyridyl-methyl 1R, cis 2,2-dimethyl-3-(2,2-dichlorovinyl)-cyclopropane-1-carboxylate 10.4 g of the product of Step A of Example 5 was subjected to chromatography to obtain 2.97 g of (S)α-cyano-6-phenoxy-2-pyridyl-methyl 1R, cis 2,2-dimethyl-3-(2,2-dichlorovinyl)-cyclopropane-1-carboxylate with a specific rotation of $[\alpha]_D^{20} = +24°$ (c=4% in toluene).

NMR Spectrum (deuterochloroform):

Peaks at 1.20–1.27 ppm (hydrogens of geminal methyls); at 6.3 ppm (hydrogen on carbon attached to —CN); at 6.14–6.23 ppm (ethylenic hydrogen); 1.87–1.97 ppm (1-hydrogen of cyclopropyl); at 6.89–7.88 ppm (hydrogens of aromatic ring).

For analysis, 2.92 g of the product were chromatographed over silica gel and were eluted with methylene chloride to obtain 2.307 g of the said product.

Analysis: $C_{21}H_{18}O_3Cl_2N_2$; molecular weight=417.89. Calculated: %C 60.44; %H 4.34; %N 6.71; %Cl 16.99. Found: %C 60.2; %H 4.4; %N 6.6; %Cl 17.1.

STEP B: (S)α-cyano-6-phenoxy-2-pyridyl-methyl 1R, cis 2,2-dimethyl-3-(1,2-dibromo-2,2-dichloroethyl)-cyclopropane-1-carboxylate Using the procedure of Example 1, the product of Step A was brominated to obtain (S)α-cyano-6-phenoxy-2-pyridyl-methyl 1R, cis 2,2-dimethyl-3-(1,2-dibromo-2,2-dichloroethyl)-cyclopropane-1-carboxylate with a specific rotation of $[\alpha]_D^{20} = -6°$ (c=0.7% in benzene).

Analysis: $C_{21}H_{18}Br_2Cl_2N_2O_3$; molecular weight=577.11. Calculated: %C 43.70; %H 3.14; %Br 27.69; %Cl 12.28; %N 4.85. Found: %C 44.0; %H 3.3; %Br 27.6; %Cl 12.1; %N 4.9.

NMR Spectrum (deuterochloroform):

Peaks at 1.21–1.25–1.32–1.38 ppm (hydrogens of geminal methyls); at 1.83–2.30 ppm (1- and 3-hydrogens of pyridyl); at 4.88–5.07–5.18–5.37 ppm (1-hydrogen of ethyl chain); at 6.30–6.31 ppm (hydrogen on carbon attached to —CN); at 6.72–7.88 ppm (hydrogens of aromatic ring).

IR Spectrum (chloroform):

Absorption at 1742 cm$^{-1}$ (ester carbonyl); at 1593, 1574 cm$^{-1}$, 1490 cm$^{-1}$ and 1450 cm$^{-1}$ (aromatic ring); at 1392 cm$^{-1}$ and 1383 cm$^{-1}$ (geminal methyls).

EXAMPLE 8

(RS)α-cyano-6-phenoxy-2-pyridyl-methyl 1R, trans, 2,2-dimethyl-3-(1,2-dibromo-2,2-dichloroethyl)-cyclopropane-1-carboxylate 1 ml of pyridine and 1 ml of (RS)α-cyano-6-phenoxy-2-pyridyl-methanol were added at 5° C. to a solution of 2.2 g of 1R, trans 2,2-dimethyl-3-(1,2-dibromo-2,2-dichloroethyl)-cyclopropane-1-carboxylic acid chloride in 22 ml of benzene and the mixture was stirred at 20° C. for 17 hours and was then poured into aqueous 0.1 N hydrochloric acid. The mixture was extracted with benzene and the organic phase was washed with water, dried and evaporated to dryness under reduced pressure to obtain raw (RS)α-cyano-6-phenoxy-2-pyridyl-methyl 1R, trans 2,2-dimethyl-3-(1,2-dibromo-2,2-dichloroethyl)-cyclopropane-1-carboxylate.

The said product was chromatographed over silica gel to obtain (R)α-cyano-6-phenoxy-2-pyridyl-methyl 1R, trans 2,2-dimethyl-3-(1,2-dibromo-2,2-dichloroethyl)-cyclopropane-1-carboxylate and (S)α-cyano-6-phenoxy-2-pyridyl-methyl 1R, trans 2,2-dimethyl-3-(1,2-dibromo-2,2-dichloroethyl)-cyclopropane-1-carboxylate identical to the products of Examples 3 and 4.

EXAMPLE 9

(RS)α-cyano-6-phenoxy-2-pyridyl-methyl 1R, trans 2,2-dimethyl-3-(1,2,2,2-tetrabromoethyl)-cyclopropane-1-carboxylate 1 ml of pyridine was added with stirring at 0° C. to a solution of 3.2 g of 1R, trans 2,2-dimethyl-3-(1,2,2,2-tetrabromoethyl)-cyclopropane-1-carboxylic acid chloride in 40 ml of toluene and then a solution of 1 g of (RS)α-cyano-6-phenoxy-2-pyridyl-methanol in 10 ml of toluene was added thereto with stirring at 0° C. The mixture was stirred at 20° C. for 17 hours and was then poured into ice. The decanted organic phase was washed with aqueous 0.1 N hydrochloric acid solution and then with water, was dried and evaporated to dryness under reduced pressure. The residue was chromatographed over silica gel to obtain (RS)α-cyano-6-phenoxy-2-pyridyl-methyl 1R, trans 2,2-dimethyl-3-(1,2,2,2-tetrabromoethyl)-cyclopropane-1-carboxylate.

Chromatography of the latter product yielded (R)α-cyano-6-phenoxy-2-pyridyl-methyl 1R, trans 2,2-dimethyl-3-(1,2,2,2-tetrabromoethyl)-cyclopropane-1-carboxylate with a melting point of 118° C. and a specific rotation of $[\alpha]_{20}^D = -13.5°$ (c=1% in benzene) and (S)α-cyano-6-phenoxy-2-pyridyl-methyl 1R, trans 2,2-dimethyl-3-(1,2,2,2-tetrabromoethyl)-cyclopropane-1-carboxylate with a specific rotation of $[\alpha]_D^{20}$=substantially 0° (c=1% in benzene).

Analysis: (R) isomer; $C_{21}H_{18}Br_4N_2O_3$; molecular weight=666.02. Calculated: %C 37.9; %H 2.7; %Br 48; %N 4.2. Found: %C 38.2; %H 2.8; %Br 47.3; %N 4.2.

NMR Spectrum (deuterochloroform): R isomer

Peaks at 1.30–1.40 ppm (hydrogens of geminal methyls); at 4.23–4.41 ppm and 4.45–4.61 ppm (1-hydrogen of ethyl side chain); at 6.30–6.33 ppm (hydrogen on carbon attached to —CN); at 7.58–7.71–7.85 ppm and 7.61–7.75–7.88 ppm (4-hydrogen of pyridyl).

NMR Spectrum (deuterochloroform): (S) isomer

Peaks at 1.21–1.35 ppm and 1.25–1.35 ppm (hydrogens of geminal methyls); at 1.71–1.80 ppm and 2.03–2.38 ppm (1- and 3-hydrogens of cyclopropyl); at 4.26–4.43 ppm and 4.43–4.60 ppm (1-hydrogen of ethyl chain); at 6.33 ppm (hydrogen of carbon attached to —CN); at 6.83–6.97 ppm (3- or 5-hydrogens of pyridyl); at 7.63–7.75–7.80 ppm (4-hydrogen of pyridyl).

EXAMPLE 10

(S)α-cyano-6-phenoxy-2-pyridyl-methyl 1R, cis 2,2-dimethyl-3-(1,2,2,2-tetrabromoethyl)-cyclopropane-1-carboxylate and
(R)α-cyano-6-phenoxy-2-pyridyl-methyl 1R, cis 2,2-dimethyl-3-(1,2,2,2-tetrabromoethyl)-cyclopropane-1-carboxylate STEP A: (RS)α-cyano-6-phenoxy-2-pyridyl-methyl 1R, cis 2,2-dimethyl-3-(1,2,2,2-tetrabromoethyl)-cyclopropane-1-carboxylate 1 ml of pyridine was added at 0° C. to a solution of 2.7 g of 1R, cis 2,2-dimethyl-3-(1,2,2,2-tetrabromoethyl)-cyclopropane-1-carboxylic acid chloride in 30 ml of toluene and 1 g of (RS)α-cyano-6-phenoxy-2-pyridyl-methanol was added thereto with stirring. The mixture was stirred at 20° C. for 16 hours and was then washed with water, with aqueous 0.1 N hydrochloric acid and with water, was dried and evaporated to dryness under reduced pressure. The residue was chromatograped over silica gel and was eluted to obtain (RS)α-cyano-6-phenoxy-2-pyridyl-methyl 1R, cis 2,2-dimethyl-3-(1,2,2,2-tetrabromoethyl)-cyclopropane-1-carboxylate.

STEP B: (R)α-cyano-6-phenoxy-2-pyridyl-methyl 1R, cis 2,2-dimethyl-3-(1,2,2,2-tetrabromoethyl)-cyclopropane-1-carboxylate The product of Step A was chromatographed over silica gel and was eluted with a 9-1 benzene-petroleum ether (b.p.=40°–70° C.) mixture to obtain (R)α-cyano-6-phenoxy-2-pyridylmethyl 1R, cis 2,2-dimethyl-3-(1,2,2,2,-tetrabromoethyl)-cyclopropane-1-carboxylate with a specific rotation of $[\alpha]_D^{20} = -31°$ (c—0.6% in benzene).

NMR Spectrum (deuterochloroform):

Peaks at 1.26–1.40–1.45 ppm (hydrogens of geminal methyls); at 1.90–2.10 ppm (1- and 3-hydrogens of cyclopropane); at 4.91–5.16 ppm and 5.16–5.41 ppm (1-hydrogen of ethyl chain); at 6.26–6.35 ppm (hydrogen on carbon attached to —CN); at 6.80–6.90 ppm (3- and 5-hydrogens of pyridyl); at 6.90–7.50 ppm (hydrogens of phenoxy).

STEP C: (S)α-cyano-6-phenoxy-2-pyridyl-methyl 1R, cis 2,2-dimethyl-3-(1,2,2,2-tetrabromoethyl)-cyclopropane-1-carboxylate The elution of Step B also yielded (S)α-cyano-6-phenoxy-2-pyridyl-methyl 1R, cis 2,2-dimethyl-3-(1,2,2,2-tetrabromoethyl)-cyclopropane-1-carboxylate with a specific rotation of $[\alpha]_D^{20} = +22.5°$ (c=1% in benzene).

NMR Spectrum (deuterochloroform):

Peaks at 1.25–1.34 ppm and 1.25–1.40 ppm (hydrogens of geminal methyls); at 4.80–5.10 ppm and 5.10–5.40 ppm (1-hydrogen of ethyl chain); at 6.30 ppm (hydrogen on carbon attached to —CN); at 6.8–6.95 ppm (3- and 5-hydrogens of pyridyl); at 7.60–7.70–7.90 ppm (4-hydrogen of pyridyl).

EXAMPLE 11

An emulsifiable concentrate was made by homogenously mixing 2.0 g of (RS)α-cyano-6-phenoxy-2-pyridyl-methyl dl, cis trans 2,2-dimethyl-3-[1(RS), 2-dibromo-2,2-dichloroethyl]-cyclopropane-1-carboxylate, 0.50 g of Tween 80, 0.10 g of Topanol A and 97.4 g of water.

A second emulsifiable concentrate was prepared by homogenously mixing 1.5 g of (RS) α-cyano-6-phenoxy-2-pyridyl-methyl 1R, trans 2,2-dimethyl-3-[1(RS), 2-dibromo-2,2-dichloroethyl]-cyclopropane-1-carboxylate, 20.0 g of Tween 80, 0.1 g of Topanol A and 78.4 g of water.

INSECTCIDICAL ACTIVITY

The insecticidal activity was illustrated for (RS) α-cyano-6-phenoxy-2-pyridyl-methyl dl cis trans 2,2-dimethyl-3-[1(RS), 2-dibromo-2,2-dichloroethyl]-cyclopropane-1-carboxylate (compound A).

A. Lethal activity against houseflies 50 female houseflies 4 days old received a topical application of 1 μl of an acetone solution of compound A on the dorsal thorax with the aid of an Arnold micromanipulator and the number of dead flies was determined 24 hours later. The results expressed as the $DL_{50}$ in nanograms which is the dose which killed 50% of the insects was 46.6 ng. This showed that compound A had interesting insecticidal activity against houseflies.

B. Knockdown activity against houseflies 50 4 day old female houseflies were directly sprayed in a Kearns and March chamber with a solution of compound A in an equal volume of kerosene and acetone (amount of solution used was 2×0.2 ml). The number of flies knocked down was determined after 10 minutes and then 15 minutes and the results expressed as $KT_{50}$ was 4.38 minutes for compound A which means it has a good knockdown activity against houseflies.

C. Insecticidal activity against *Blattella germanica*

Adult males of *Blattella germanica* received a topical application of 2 μl of an acetone solution of compound A between the second and third pairs of feet and the insects were kept in dim light at 20° C. and were fed. The doses of compound A were 10, 7.5, 3.75 and 2.5 ng per insect and the number of dead were determined at 24 and 48 hours and 6 days after treatment to determine the $DL_{50}$ which was 4.2 ng per insect. This shows that compound A has a good insecticidal activity against *Blattella germanica*.

D Insecticidal activity against *Spodoptera Littoralis* caterpillars

15 *Spodoptera Littoralis* caterpillers in the 4th larva stage received a topical application of 1 μl of an acetone solution of compound A on the dorsal thorax of each and after treatment, the caterpillars were placed in an artificial nutritive medium (Poitoit medium). The percentage of dead compared to non-treated controls after 24 and 48 hours was used to determine the $DL_{50}$ which was 44.6 ng per caterpillar. This shows that compound A has an interesting insecticidal activity against *Spodoptera Littoralis* larvae.

E. Insecticidal activity against *Epilachna varivestris* larvae

The test was analogous to that of test D and the *Epilachna varivestris* larvae used were in the last stage of larva development. After treatment, the larvae were fed bean plants and 72 hours later the number of dead was determined. The $DL_{50}$ for compound A was 2.2 ng per insect which shows a strong insecticidal activity against *Epilachna varivestris* larvae.

F. Acaricidal activity

25 *Tetranychus urticae* acariens were placed on bean leaves having glue about their periphery and the bean leaves were divided into a first group treated by spraying with 2.5 ml of an aqueous solution of compound A per leaf at different concentrations and a second control group which was not treated. The number of acariens living 48 hours after the spraying was used to determine the $DL_{50}$ which was 5000 mg/hl which indicates an interesting activity against *Tetranychus urticae* acariens.

Various modifications of the products and methods of the invention may be made without departing from the spirit or scope thereof and it is to be understood that the invention is intended to be limited only as defined in the appended claims.

We claim:

1. An ester in the form of their stereoisomers or mixtures thereof of the formula

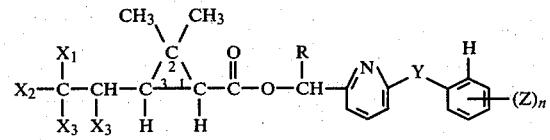

$X_1$ is selected from the group consisting of fluorine, chlorine and bromine, $X_2$ is selected from the group consisting of fluorine, chlorine and bromine, $X_3$ is selected from the group consisting of chlorine and bromine, each Z is independently selected from the group consisting of alkyl of 1 to 4 carbon atoms, alkoxy and alkylthio of 1 to 4 carbon atoms, alkylsulfonyl of 1 to 4 carbon atoms, $-CF_3$, 3,4-methylenedioxy, chlorine, fluorine and bromine, n is 0, 1 or 2, Y is selected from the group consisting of oxygen and sulfur and R is selected from the group consisting of hydrogen, $-CN$ and ethynyl, the acid moiety having a structure selected from the group consisting of 1R, cis; 1S, cis; 1R, trans; and 1S, trans and the alcohol moiety having a configuration of (R), (S) or (RS) and the asymetric carbon in the 1-position of the 3-ethyl side chain exists in the form of isomer A and isomer B.

2. A compound of claim 1 wherein R is cyano, Y is oxygen and n is 0.

3. A compound of claim 1 wherein the acid moiety has the dl cis or dl trans structure.

4. A compound of claim 1 wherein the acid moiety has the 1R, cis or 1R, trans structure.

5. A compound of claim 1 wherein $X_1$ and $X_2$ are chlorine and $X_3$ is bromine.

6. A compound of claim 1 wherein all Xs are bromine.

7. A compound selected from the group consisting of (R)α-cyano-6-phenoxy-2-pyridyl-methyl 1R, trans 2,2-dimethyl-3-(1,2,2,2-tetrabromoethyl)-cyclopropane-1-carboxylate, (S)α-cyano-6-phenoxy-2-pyridyl-methyl 1R, trans 2,2-dimethyl-3-(1,2,2,2-tetrabromoethyl)-cyclopropane-1-carboxylate, (R)α-cyano-6-phenoxy-2-pyridyl-methyl 1R, cis 2,2-dimethyl-3-(1,2,2,2-tetrabromoethyl)-cyclopropane-1-carboxylate, (S)α-cyano-6-phenoxy-2-pyridyl-methyl 1R, cis 2,2-dimethyl-3-(1,2,2,2,-tetrabromoethyl)-cyclopropane-1-carboxylate, (R)α-cyano-6-phenoxy-2-pyridyl-methyl 1R, trans 2,2-dimethyl-3-(1,2-dibromo-2,2-dichloroethyl)-cyclopropane-1-carboxylate, (S)α-cyano-6-phenoxy-2-pyridyl-methyl 1R, trans 2,2-dimethyl-3-(1,2-dibromo-2,2-dichloroethyl)-cyclopropane-1-carboxylate, (S)α-cyano-6-phenoxy-2-pyridyl-methyl 1R, cis 2,2-dimethyl-3-(1,2-dibromo-2,2-dichloroethyl)-cyclopropane-1-carboxylate, (R)α-cyano-6-phenoxy-2-pyridyl-methyl 1R, cis 2,2-dimethyl-3-(1,2-dibromo-2,2-dichloroethyl)-cyclopropane-1-carboxylate, (RS)α-cyano-6-phenoxy-2-pyridyl-methyl 1R, trans 2,2-dimethyl-3-(1,2,2,2-tetrabromoethyl)-cyclopropane-1-carboxylate, (RS)α-cyano-6-phenoxy-2-pyridyl-methyl 1R, cis 2,2-dimethyl-3-(1,2,2,2,-tetrabromoethyl)-cyclopropane-1-carboxylate, (RS)α-cyano-6-phenoxy-2-pyridyl-methyl 1R, trans 2,2-dimethyl-3-(1,2-dibromo-2,2-dichloroethyl)-cyclopropane-1-carboxylate, (RS)α-cyano-6-phenoxy-2-pyridyl-methyl 1R, cis 2,2-dimethyl-3-(1,2-dibromo-2,2-dichloroethyl)-cyclopropane-1-carboxylate and (RS)α-cyano-6-1-phenoxy-2-pyridyl-methyl dl cis trans 2,2-dimethyl-3-(1,2-dibromo-2,2-dichloroethyl)-cyclopropane-1-carboxylate.

8. An insecticidal composition comprising an insecticidally effective amount of a compound of claim 1 and an inert carrier.

9. A composition of claim 8 wherein R is cyano, Y is oxygen and n is 0.

10. A composition of claim 8 wherein the acid moiety has the dl cis or dl trans structure.

11. A composition of claim 8 wherein the acid moiety has the 1R, cis or 1R, trans structure.

12. A composition of claim 8 wherein $X_1$ and $X_2$ are chlorine and $X_3$ is bromine.

13. A composition of claim 8 wherein all Xs are bromine.

14. An acaricidal composition comprising an acaricidally effective amount of a compound of claim 1 and an inert carrier.

15. A composition of claim 14 wherein R is cyano, Y is oxygen and n is 0.

16. A composition of claim 14 wherein the acid moiety has the dl cis or dl trans structure.

17. A composition of claim 14 wherein the acid moiety has the 1R, cis or 1R, trans structure.

18. A composition of claim 14 wherein $X_1$ and $X_2$ are chlorine and $X_3$ is bromine.

19. A composition of claim 14 wherein all Xs are bromine.

20. A nematocidal composition comprising a nematocidally effective amount of a compound of claim 1 and an inert carrier.

21. A composition of claim 20 wherein R is cyano, Y is oxygen and n is 0.

22. A composition of claim 20 wherein the acid moiety has the dl cis or dl trans structure.

23. A composition of claim 20 wherein the acid moiety has the 1R, cis or 1R, trans structure.

24. A composition of claim 20 wherein $X_1$ and $X_2$ are chlorine and $X_3$ is bromine.

25. A composition of claim 20 wherein all Xs are bromine.

26. A fungicidal composition comprising a fungicidally effective amount of a compound of claim 1 and an inert carrier.

27. A composition of claim 26 wherein R is cyano, Y is oxygen and n is 0.

28. A composition of claim 26 wherein the acid moiety has the dl cis or dl trans structure.

29. A composition of claim 26 wherein the acid moiety has the 1R, cis or 1R, trans structure.

30. A composition of claim 26 wherein $X_1$ and $X_2$ are chlorine and $X_3$ is bromine.

31. A composition of claim 26 wherein all Xs are bromine.

32. A method of combatting acariens comprising contacting acariens with an acaricidally effective amount of a compound of claim 1.

33. A method of claim 32 wherein R is cyano, Y is oxygen and n is 0.

34. A method of claim 32 wherein the acid moiety has the dl cis or dl trans structure.

35. A method of claim 32 wherein the acid moiety has the 1R, cis or 1R, trans structure.

36. A method of claim 32 wherein $X_1$ and $X_2$ are chlorine and $X_3$ is bromine.

37. A method of claim 32 wherein all Xs are bromine.

38. A method of combatting insects comprising contacting insects with an insecticidally effective amount of at least one compound of claim 1.

39. A method of claim 38 wherein R is cyano, Y is oxygen and n is 0.

40. A method of claim 38 wherein the acid moiety has the dl cis or dl trans structure.

41. A method of claim 38 wherein the acid moiety has the 1R, cis or 1R, trans structure.

42. A method of claim 38 wherein $X_1$ and $X_2$ are chlorine and $X_3$ is bromine.

43. A method of claim 38 wherein all Xs are bromine.

44. A method of combatting nematodes comprising contacting nematodes with a nematocidally effective amount of a compound of claim 1.

45. A method of claim 44 wherein R is cyano, Y is oxygen and n is 0.

46. A method of claim 44 wherein the acid moiety has the dl cis or dl trans structure.

47. A method of claim 44 wherein the acid moiety has the 1R, cis or 1R, trans structure.

48. A method of claim 44 wherein $X_1$ and $X_2$ are chlorine and $X_3$ is bromine.

49. A method of claim 44 wherein all Xs are bromine.

50. A method of combatting fungi comprising contacting fungi with a fungidically effective amount of a compound of claim 1.

51. A method of claim 50 wherein R is cyano, Y is oxygen and n is 0.

52. A method of claim 50 wherein the acid moiety has the dl cis or dl trans structure.

53. A method of claim 50 wherein the acid moiety has the 1R, cis or 1R, trans structure.

54. A method of claim 50 wherein $X_1$ and $X_2$ are chlorine and $X_3$ is bromine.

55. A method of claim 50 wherein all Xs are bromine.

* * * * *

UNITED STATES PATENT AND TRADEMARK OFFICE
CERTIFICATE OF CORRECTION

PATENT NO. : 4,315,012

DATED : February 9, 1982

INVENTOR(S) : JACQUES MARTEL ET AL.

It is certified that error appears in the above—identified patent and that said Letters Patent is hereby corrected as shown below:

Title page [54], and Column 1, lines 1 and 2: The title should read as follows:

-- NOVEL 3-TETRAHALOETHYL-CYCLOPROPANE-1-CARBOXYLATE ESTERS --

Column 2, line 57; Column 3, line 8; Column 7, lines 7 and 40; Column 10, line 55; Column 14, lines 39 and 44:

"dichloroe-" should read -- dichloro- --.

Column 2, line 58; Column 3, lines 9, 14, 27 and 33; Column 7, lines 8 and 41; Column 10, line 56; Column 14, lines 40 and 45:

"thyl" should read -- ethyl --.

Column 3, line 2: "lcarboxylate" should read -- 1-carboxylate --

Column 3, line 13: "dibromoe-" should read -- dibromo- --.

Column 3, line 26: "chloroe-" should read -- chloro- --.

Column 3, line 32: "fluoroe-" should read -- fluoro- --.

Column 5, line 28: "butox-" should read -- butoxy- --

Column 5, line 29" "yethoxy" should read -- ethoxy --.

Column 7, line 38; Column 8, line 15:

"on CN" should read -- to CN ---

UNITED STATES PATENT AND TRADEMARK OFFICE
CERTIFICATE OF CORRECTION

PATENT NO. : 4,315,012

DATED : February 9, 1982

INVENTOR(S) : JACQUES MARTEL ET AL.

It is certified that error appears in the above—identified patent and that said Letters Patent is hereby corrected as shown below:

Column 14, line 43: "6-1-phenoxy" should read
-- 6-phenoxy --.

Column 16, line 6: "at least one compound" should read
-- a compound --.

Signed and Sealed this

First Day of June 1982

[SEAL]

Attest:

GERALD J. MOSSINGHOFF

Attesting Officer    Commissioner of Patents and Trademarks